United States Patent [19]

Pfirmann et al.

[11] Patent Number: 5,227,535
[45] Date of Patent: Jul. 13, 1993

[54] PROCESS FOR THE PREPARATION OF 2-NITRO-5-FLUORO- OR -5-CHLOROPHENOL

[75] Inventors: Ralf Pfirmann, Griesheim; Theodor Papenfuhs, Frankfurt am Main; Klaus Forstinger, Kelsterbach, all of Fed. Rep. of Germany

[73] Assignee: Hoechst Aktiengesellschaft, Frankfurt am Main, Fed. Rep. of Germany

[21] Appl. No.: 957,674

[22] Filed: Oct. 7, 1992

[30] Foreign Application Priority Data

Oct. 9, 1991 [DE] Fed. Rep. of Germany ....... 4133447

[51] Int. Cl.$^5$ .......................................... C07C 205/20
[52] U.S. Cl. ................................................... 568/709
[58] Field of Search ................................. 568/709, 713

[56] References Cited

U.S. PATENT DOCUMENTS

| | | | |
|---|---|---|---|
| 3,461,173 | 4/1969 | Peterson | 568/709 |
| 3,928,470 | 12/1975 | Soula et al. | 568/709 |
| 4,310,711 | 1/1982 | Müller et al. | 568/709 |

FOREIGN PATENT DOCUMENTS 2614264  6/1977  Fed. Rep. of Germany ...... 568/709

*Primary Examiner*—Werren B. Lone
*Attorney, Agent, or Firm*—Connolly and Hutz

[57] ABSTRACT

The present invention relates to a process for the preparation of isomerically pure 2-nitro-5-fluoro- or -5-chlorophenol, by reacting 2,4-difluoronitrobenzene or 2,4-dichloronitrobenzene with aqueous alkali metal or alkaline earth metal hydroxide solution or suspension in the absence of organic solvents or other solubility promoting substances at temperatures from about 20° C. to about 190° C., adjusting the pH of the reaction mixture to about 1 to about 6 by the addition of acid, steam distilling the resultant product and isolating it from the distillate after cooling.

11 Claims, No Drawings

PROCESS FOR THE PREPARATION OF 2-NITRO-5-FLUORO- OR -5-CHLOROPHENOL

DESCRIPTION

The present invention relates to an improved process for the preparation of 2-nitro-5-fluoro- or -5-chlorophenol in good yields and with high selectivity. The compounds represent valuable precursors for the preparation of crop protection agents and pharmaceuticals.

It is known that the fluorine compound mentioned may be prepared over long reaction times (32 hours) in ethers such as dioxane, using phase transfer catalysis at low temperatures (30° C.) (JP 63310851 A2). Working in water produces an isomeric ratio of about 7:1. Nothing is known from this source about the separation of the isomers. Furthermore, it is known that the chlorine compound may also be prepared in solvent/water mixtures in yields of about 90% (DE 29 39 056). In an earlier known process (DE 29 35 629) aqueous alkali metal hydroxide solutions are used in polar aprotic solvents and emulsifiers (20 hours, 60° C., 81%) for this reaction. Finally it is known that in general 2-nitrohalophenols may be prepared by the reaction of the corresponding nitrohalobenzenes at high temperatures (155° C., 2 hours) in anhydrous media. 4,5-dichloro-2-nitrophenol may be obtained in 77% yield in this way (DE 26 14 264). 2-nitro-5-chlorophenol may be obtained by reacting 4-chloronitrobenzene with KOH at 50° C. in the presence of glass bodies (FR 1 581 400). The same oxidation may be performed in 85–87% yield in solvents, for example 1,2-dimethoxyethane, using phase transfer catalysis (18-crown-6) (Izv. Akad. Nauk. SSSR, Ser. Khim., (11) 2635–2636). Yields of about 90% may be obtained in tertiary alcohols when using aqueous potassium hydroxide solution (6 hours, 60° C.) (JP 52142031). Nitration of 3-chlorophenol has long been known (Uhlemann, Chem. Ber. (1878), 1161; De Kiewiet, Stephen, J. Chem. Soc. (1931), 84). This nitration may also be performed in acetic acid at 0° C. (Roberts, Rhys, J. Chem. Soc. (1937), 39, 41) or using sodium nitrate and dilute sulfuric acid (Hodgson, Moore, J. Chem. Soc. 127 (1925), 1600). A variant is the reaction of 3-chloroaniline with dilute nitric acid (Uhlemann, loc. cit.) or gases containing nitrogen oxides ($NO_x$); however, isomers are produced besides the desired product (v. Auwers, Deines, Fortschr. Ch. Phys. 18, 59; Chem. Zentralblatt, 1924 (II) 2268). In addition, reactions of 4-chloro-1,2-dinitrobenzene with aqueous alkali metal hydroxide solution (Laubenheimer, Chem. Ber. 9 (1876), 768) and of 2-nitro-5-aminophenol with copper(I) chloride in the sense of a Sandmeyer reaction (Phillips, J. Chem. Soc. (1930), 1910, 1913) are known, 2-nitro-5-chlorophenol being obtained.

Since 2-nitro-5-fluoro- and -5-chlorophenol can be converted, by methods which are disclosed in the literature, into herbicides (EP 304409 A1, JP 63310851 A2, U.S. Pat. No. 4 734 124), insecticides (DuPont de Nemours, E.I. & Co., WO 9003378 A1), hair colorants (DE 35 33 792 A1), pharmacologically active substances, such as lipoxygenase inhibitors (EP 262 618 A2) or blood pressure regulators (DE 35 24 635 A1) or antibacterially active substances (U.S. Pat. No. 3 461 173, U.S. Pat. No. 3 551 503) and in addition a fungicidal activity has already been detected for the compounds in question (R. H. Shiley, J. L. Forsberg, R. S. Perry, D. R. Dickerson, G. C. Finger, J. Fluorine Chem., 5(4), 371–376), there was a need to be able to prepare these compounds by a new, improved and economical process which was as simple as possible.

It has now been found that isomerically pure 2-nitro-5-fluoro- or -5-chlorophenol may advantageously be prepared in good to very good yields and with high selectivity by reacting 2,4-difluoronitrobenzene or 2,4-dichloronitrobenzene with aqueous alkali metal hydroxide solution or alkline earth metal hydroxide solution or suspension, preferably sodium hydroxide solution or potassium hydroxide solution, in the absence of organic solvents or other solubilizers at temperatures from about 20° C. to about 190° C., preferably from about 20° C. to about 70° C in the case of 2,4-difluoronitrobenzene, and from about 100° C. to about 160° C. in the case of 2,4-dichloronitrobenzene, adjusting the pH of the reaction mixture to about 1 to about 6, preferably to about 1.5 to about 3.0, by the addition of acid, steam distilling the resultant product by passing steam into the reaction mixture, and isolating the product from the distillate after cooling.

At no stage in the process according to the invention is an organic solvent present.

In the course of performing the process in detail it is also possible to filter off under suction the precipitated product which is obtained after the acidifying stage and not to subject it to steam distillation until afterwards. This has the advantage, in the case of the fluorine compound, that the hydrofluoric acid may be removed before the steam is introduced. Otherwise, corrosion of the apparatus being used may be maintained at a low level by the addition of fluoride scavengers. Suitable agents for this purpose are calcium salts such as for example calcium chloride, calcium sulfate, calcium hydroxide or silicon dioxide, silicon dioxide with an enlarged internal surface area being particularly preferred, or tributyltin compounds such as for example tri-n-butyltin chloride. These fluoride scavengers are used in amounts which are about 0.5 to about 10 times, preferably about 1.5 to about 4 times, the amount of fluoride which is produced in theory. It was surprising that even in the dilute aqueous solution produced in the process according to the invention it was possible to substantially suppress the corrosion due to hydrofluoric acid.

The process according to the invention may also be performed in detail in such a way that acidification takes place gradually during the steam distillation. This is particularly gentle on the apparatus materials and the product may nonetheless be isolated in good to very good yields.

To obtain high selectivity and to ensure stirrability of the solution during reaction, it is expedient to add the alkali metal hydroxide solution or alkaline earth metal hydroxide solution to a mixture of 2,4-difluoronitrobenzene or 2,4-dichloronitrobenzene which is already present. In the case of the chlorine compound, this procedure need not be used. The same effect is produced if the reaction partners are introduced first and the reaction mixture is heated up slowly.

The process according to the invention produces 2-nitro-5-fluorophenol in isomerically pure form in 78% yield, while 2-nitro-5-chlorophenol may be obtained in 91% yield. The process is expediently performed at atmospheric pressure. However, the reaction may also take place under excess pressure, as proves necessary during reaction of 2,4-dichloronitrobenzene using the process according to the invention in order to obtain sufficiently rapid reaction.

Aqueous alkali metal hydroxide solutions which may be used are for example lithium, sodium, potassium, rubidium or cesium hydroxide solutions or mixtures thereof, preferably sodium or potassium hydroxide solutions, and alkaline earth metal hydroxide solutions which may be used are for example magnesium, calcium, strontium or barium hydroxide solutions or mixtures thereof, preferably calcium hydroxide solutions. The hydroxides mentioned are used in the form of about 10 to about 80% strength solutions, preferably about 30 to about 50% strength solutions. Equally expedient is the use of suspensions of the corresponding alkali metal hydroxides or alkaline earth metal hydroxides instead of the previously mentioned solutions if it is not possible to dissolve these in the particular amount of water which is used.

Acidification may take place using conventional non-oxidizing mineral acids, such as for example dilute sulfuric acid, phosphoric acid, hydrochloric acid, hydrobromic acid or hydroiodic acid, and with sufficiently strong organic acids such as for example formic acid or acetic acid.

The process according to the invention is described in more detail in the following examples, but this does not represent a limitation.

EXAMPLE 1

159.1 g (1 mol) of 2,4-difluoronitrobenzene and 550 g of water are initially introduced and are heated to 55° C. With vigorous stirring, 241.2 g (2.15 mol) of 50% strength potassium hydroxide solution are added dropwise over 4 hours and the temperature is maintained at 55° C. (exothermic reaction). Stirring is then continued for another 2 hours at this temperature. The pH is then adjusted to 4.3 (25° C.) using 88 g of sulfuric acid, and 74.1 g of calcium hydroxide are added. The pH is readjusted to 5.0 and the introduction of steam is started. During distillation the pH is decreased from 5 to 1.5 by dropwise addition of sulfuric acid. The product is isolated by cooling and filtering the distillate. After drying, 117.9 g (0.750 mol, 75% of theory) of bright yellow 2-nitro-5-fluorophenol is obtained, which is more than 99.9% pure according to GC and HPLC (solidification point 32.1° C.).

If sodium hydroxide is used instead of potassium hydroxide and/or if acidification is with hydrochloric acid instead of sulfuric acid and/or if calcium chloride is used instead of calcium hydroxide as fluoride scavenger, then essentially the same result is obtained.

EXAMPLE 2

59.1 g (1 mol) of 2,4-difluoronitrobenzene and 300 g of water are initially introduced and 52.7 g (2.2 mol) of 50% strength lithium hydroxide solution are added dropwise at 45° C. The temperature is allowed to rise to 55° C. as a result of the exothermic reaction. After the end of this addition (5 hours) 60.1 g of silicon dioxide (Aerosil) are added and the pH is adjusted to 1.5 with sulfuric acid. The product is distilled over by the introduction of steam and isolated as described in example 1. 115.5 g (0.735 mol, 74% of theory) of 2-nitro-5-fluorophenol are obtained, which do not differ from the material prepared by example 1 with respect to purity.

Lithium carbonate may be used instead of lithium hydroxide to produce the same result. If phosphoric acid is used instead of sulfuric acid to acidify the reaction mixture then essentially the same result is obtained.

EXAMPLE 3

749.6 g (2.12 mol) of 20% strength cesium hydroxide solution are added dropwise to 159.1 g (1 mol) of 2,4-difluoronitrobenzene at 40° C. over the course of 6 hours, and the mixture is then stirred for a further 1 hour. The pH is adjusted to 2 with 85% strength phosphoric acid and the product is distilled over using steam (1.5 hours). After working up, as described in example 1, 120.2 g (0.765 mol, 77% of theory) of 2-nitro-5-fluorophenol are obtained (purity (GC) > 99.9%).

If hydrobromic acid is used instead of phosphoric acid for acidifying, then essentially the same result is obtained.

EXAMPLE 4

192.0 g (1 mol) of 2,4-dichloronitrobenzene, 600 g of water and 273.0 g (2.05 mol) of sodium hydroxide are heated to 140° C. in a VA steel autoclave with vigorous stirring for 6 hours. The reacted reaction mixture is removed from the autoclave at 70° C. The orange-brown solution produced is adjusted to pH 2 using 30% strength hydrochloric acid, and the product is distilled over using steam. On stirring the distillate (about 1.5 l) at 10° C, 2-nitro-5-chlorophenol (156.4 g, 90% of theory) is obtained in the form of yellow crystals.

If the mixture is acidified to pH 2 with formic acid instead of 30% strength hydrochloric acid, then essentially the same result is obtained. Sodium carbonate may be used instead of sodium hydroxide, in the same amount, without essentially changing the result.

EXAMPLE 5

192.0 g (1 mol) of 2,4-dichloronitrobenzene, 750 g of water and 185.3 g (2.5 mol) of calcium hydroxide are heated to 150° C. under pressure for 14 hours. The undissolved components are subsequently filtered off at 70° C. The filtrate is adjusted to pH 1 using hydroiodic acid and the product is distilled over using steam. On stirring the distillate, 2- nitro-5-chlorophenol (151.0 g, 87% of theory) which has a purity of more than 99.9% (GC, HPLC) is obtained.

If the mixture is acidified to pH 2.5 with acetic acid instead of hydroiodic acid, then essentially the same result is obtained. Calcium carbonate may be used instead of calcium hydroxide, in the same amount, without essentially changing the result.

We claim:

1. A process for the preparation of isomerically pure 2-nitro-5-fluoro- or -5-chlorophenol, wherein 2,4-difluoronitrobenzeneor2,4-dichloronitrobenzene is reacted with aqueous alkali metal hydroxide solution or alkaline earth metal hydroxide solution or suspension in the absence of organic solvents or other solubilizers at temperatures from about 20° C. to about 190° C., the pH of the reaction mixture is adjusted to about 1 to about 6 by the addition of acid, the resultant product is steam distilled and is isolated from the distillate after cooling.

2. The process as claimed in claim 1, wherein 2,4-difluoronitrobenzene is reacted at temperatures from about 40° C. to about 70° C.

3. The process as claimed in claim 1, wherein 2,4-dichloronitrobenzene is reacted at temperatures from about 100° C. to about 160° C.

4. The process as claimed in claim 1, wherein the pH of the reaction mixture is adjusted to about 1.5 to about 3.0.

5. The process as claimed in claim 1, wherein the aqueous alkali metal hydroxide solution used is aqueous lithium, sodium, potassium, rubidium or cesium hydroxide solution or mixtures thereof.

6. The process as claimed in claim 1, wherein the aqueous alkaline earth metal hydroxide solution used is aqueous magnesium, calcium, strontium or barium hydroxide solution or mixtures thereof.

7. The process as claimed in claim 1, wherein acidification of the reaction takes place using a non-oxidizing mineral acid.

8. The process as claimed in claim 1, wherein acidification of the reaction takes place during steam distillation in parallel with discharge of the product.

9. The process as claimed in claim 1, wherein fluoride scavengers are added to the reacted reaction mixture before acidification.

10. The process as claimed in claim 1, wherein the fluoride scavengers used before acidifying the reacted reaction mixture are calcium chloride, calcium sulfate, hydroxide or silicon dioxide or tributyltin compounds.

11. The process as claimed in claim 1, wherein the process is performed at atmospheric or excess pressure.

* * * * *